United States Patent [19]

Subramanian

[11] Patent Number: 5,244,816
[45] Date of Patent: Sep. 14, 1993

[54] METHOD FOR PURIFYING CHELATOR CONJUGATED COMPOUNDS

[75] Inventor: Ramaswamy Subramanian, Frederick, Md.

[73] Assignee: Akzo N.V., Arnhem, Netherlands

[21] Appl. No.: 419,871

[22] Filed: Oct. 11, 1989

[51] Int. Cl.$^5$ .......................................... G01N 33/534
[52] U.S. Cl. .................... 436/545; 436/544; 436/547; 436/548; 436/804
[58] Field of Search ............... 436/544, 545, 546, 547, 436/548, 804

[56] References Cited

U.S. PATENT DOCUMENTS

| | | | |
|---|---|---|---|
| 4,283,382 | 8/1981 | Frank et al. | 436/546 |
| 4,320,111 | 3/1982 | Hirsch et al. | 435/4 |
| 4,454,106 | 6/1984 | Gansow et al. | 436/548 |
| 4,472,509 | 9/1984 | Gansow et al. | 436/548 |
| 4,652,440 | 3/1987 | Paik et al. | 424/9 |
| 4,668,503 | 5/1987 | Huatowich | 436/548 |
| 4,707,352 | 11/1987 | Stavrianpoulos | 424/1.1 |
| 4,775,638 | 10/1988 | Haisma | 436/808 |
| 5,057,302 | 10/1991 | Johnson et al. | 435/7.92 |

FOREIGN PATENT DOCUMENTS 264333 4/1988 European Pat. Off. .

OTHER PUBLICATIONS

D. Huatowich et al., Chem. Abst., vol. 108, No. 108851r (1988).
O. Gansow et al., Chem. Abst., vol. 100, No. 126881q (1984).
A. Lockshin et al., E. J. Nucl. Med., vol. 12, pp. 573-575 (1987).
Esteban et al., J. Nucl. Med. 28:861-870 (1987).
Halpern et al., J. Nucl. Med. 29:1688-1696 (1988).
Mukkala et al., Analytical Biochemistry (176) 319-325 (1989).

*Primary Examiner*—Mary E. Ceperley
*Attorney, Agent, or Firm*—William M. Blackstone

[57] ABSTRACT

A method for removing unbound labeling reagent from a composition comprising bound and unbound labeling reagent is described. Lilo-matrix conjugate capable of binding unbound labeling reagent is contacted with a biomolecule labeling reaction mixture and then the labeled biomolecule essentially free of unbound labeling reagent is removed.

19 Claims, 4 Drawing Sheets

METHOD FOR PURIFYING CHELATOR CONJUGATED COMPOUNDS

FIELD OF INVENTION

The invention relates to the labeling of biomolecules. More specifically, the invention relates to the separation of labeled biomolecules from unbound labeling reagent following the labeling reaction. The invention has particular relevance when the biomolecule is a protein and the labeling reagent is a radionuclide. Particular applications lie in the fields of immunodiagnostics and immunotherapy.

BACKGROUND OF THE INVENTION

Biomolecules can be labeled with any of a variety of reagents, including radionuclides, toxins, vitamins, fluorescent compounds and chelating agents. A labeling reagent may be incorporated as a constituent of a biomolecule, for example by metabolic labeling or by nick translation, or may be attached to a biomolecule by a covalent bond or another intermolecular force. Examples of the latter category of labeling method include the use of isothiocyanate derivatives of fluorochromes to render antibodies fluorescent, the use of photoactive derivatives of biotin to label nucleic acids and the use of oxidative or enzyme-mediated reactions to attach iodine onto proteins at tyrosine residues. The labeling procedure can be as simple as mixing a biomolecule and a labeling reagent.

U.S. Pat. No. 4,707,352 discloses a labeling method which comprises the step of contacting an unlabeled compound, consisting of a chelating agent conjugated to a biomolecule, with an ion transfer material to which is bound a radiometal. The affinity of said ion transfer material for the radiometal is less than the affinity of said chelating agent for said metal. In the example a column containing an ion exchange resin loaded with $^{63}Ni$ is used. A chelator conjugate is passed through the column and eluted as the radiolabeled chelator conjugate. The components to perform the labeling method may be incorporated into kits.

At the conclusion of a labeling reaction, it is often desirable to purify the labeled biomolecule, the product, by separating any reactant, particularly unreacted labeling reagent, from said product. Presence of unbound labeling reagent can confound outcomes by associating with irrelevant molecules (non-specific binding) or by contributing to the background.

Because many labeling reagents are small molecules or elements, common methods for separating product from unbound reagent rely on size or weight differential. Thus, size exclusion chromatography or dialysis may be used. If there is a charge difference between the product and reactant, ion exchange chromatography is a suitable separation method.

A method for purifying radiolabeled antibody combining ion exchange and size exclusion resins is disclosed in U.S. Pat. No. 4,454,106. A 9 cm column is made comprising 1 ml of an ion retarding resin above 1 ml of a 200-400 mesh cation exchange resin above 7 ml of gel filtration medium capable of fractionating particles 1,500-25,000 daltons in weight. The column is equilibrated with a buffer consisting of 200 mM sodium chloride and 10 mM MES at pH 6.0. In the related U.S. Pat. No. 4,472,509, the preferred bed for purifying technetium-labeled antibodies is the three component bed described above modified to include 1 ml of an anion exchange resin situated below the cation exchange resin and above the gel filtration medium.

Mukkala et al. (Anal Biochem (1989) 176:319-325) labeled IgG with $Eu^{3+}$ using bridging chelators. The labeled antibody product was purified from the reactants by passing the reaction mixture over a combined 1.5×5 cm Sephadex G-50 (Pharmacia Fine Chemicals; dextran beads) column and a 1.5×30 cm Trisacryl GF2000 (Reactifs IBF; polyacrylamide beads) column.

Esteban et al. (J. Nucl Med (1987) 28:861-870) compared four protocols for purifiying $^{111}In$-labeled antibody at completion of the labeling procedure. They divided a single labeling preparation into four equal portions. One aliquot was treated with excess EDTA in solution without subsequent separation. Another aliquot was passed over a 1×8 cm gel exclusion (Sephadex G-50 fine) column. The third aliquot was injected onto a 7.5 mm×30 cm HPLC (TSK 3000) column and the final aliquot was treated sequentially over the G50 column and then the TSK 3000 column. The poorest results were obtained with the EDTA treatment, the G-50 column was marginally better, the HPLC-purified labeled antibody had a tumor:liver ratio three times that of the EDTA-purified aliquot and the best results were obtained with the G-50/TSK 3000 combination. The authors concluded that the widely used EDTA method was inefficient in producing clean preparations and other purification methods should be considered if one wants to minimize background.

U.S. Pat. No. 4,775,638 discloses a single vial technique for radiolabeling antibody. The method comprises introducing radioisotope into a sealed vessel in which the inner surface of said vessel is coated with a catalyst; introducing antibody into said vessel; incubating the mixture; introducing into said vessel an ion exchange resin which absorbs radioisotope not bound to antibody; withdrawing the mixture; and separating the resin from the supernatant. The preferred resin is an anion exchanger such as AG 1-X8 (Bio-Rad). Although the method is directed primarily to radio-iodination procedures, the inventor surmised that the catalyst-mediated attachment of radioisotope to antibody and the subsequent purification of said labeled antibody might be adapted for $^{67}Ga$ and $^{111}In$ labeling by chelation.

Notwithstanding the variety of separation methods available to the artisan, a systematic limitation constrains the use of labeled biomolecules in procedures demanding high sensitivity. That limitation is the sometimes low efficacy of removing unbound labeling reagent of many current methods in the art. A clear example is the use of radiolabeled anti-cancer antibodies in situ for the detection of malignant growths, a method known as radioimmunoscintigraphy. For various reasons not related directly to the instant invention, often, only a small amount of antibody binds to a malignancy. Thus, the signal is difficult to discern even under ideal conditions. It is not uncommon for diagnosis to be rendered impossible because of high background. Accordingly, one way to assure or enhance detection is using labeled antibody that is significantly free of unbound radionuclides.

A further limitation to the use of gel exclusion chromatography is the propensity of IgM antibodies to bind nonspecifically and at times irreversibly to the column matrix. See for example Halpern et al., J. Nucl Med (1988) 29:1688-1696.

Another limitation relates to the prolonged time frame of most procedures. Many of the radionuclides and particularly the radiometals have a short half-life, which if not days, often is a matter of hours. Thus rapid purification enhances the specific activity of a labeled biomolecule preparation.

Furthermore, the separation procedures recited above are not without additional shortcomings. Many require costly equipment and skilled technicians, are prone to biologic contamination, require close monitoring, are not amenable to scale-up and the like. The equipment may be difficult and costly to decontaminate in the event of radioactive spills.

Resolution of the above-noted problems provided the motivation for the instant invention. Disclosed herein is a means for obtaining a higher degree of separation of labeled product from unbound reactant than that achieved using current procedures. The instant method is advantageous for several reasons, including simplicity and inexpensiveness. Additionally the method is not prone to biologic contamination, does not affect the bioactivity of the biomolecule, offers high concentrated yields, can be used in a standard hospital laboratory by nursing staff, is easy to dispose of after use, has a long shelf life and is adaptable for use with a variety of labeling reagents and biomolecules.

SUMMARY OF THE INVENTION

The instant invention relates to a method for separating after a labeling reaction labeled biomolecules, the product, from any unbound or weakly bound labeling reagent. The invention teaches the use of chelator attached matrices to scavenge said unbound labeling reagent. The method offers several advantages, including simplicity, highly efficient removal of unbound labeling reagent and economy. The reagents to carry out the invention are readily adaptable into kit form for use in applied settings, as in hospitals and nuclear pharmacies.

DETAILED DESCRIPTION OF THE INVENTION

All of the terms used in the specification and the claims are known to one with ordinary skill in the art. Nevertheless, to provide clear and consistent understanding of the specification and claims, including the scope given to such terms, the following definitions are provided:

Biomolecule: Element or compound compatible in or with a biologic entity.

Bound: Physical attachment of labeling reagent to a biomolecule.

Chelator: Reagent that binds metal ions with high affinity. Known also as chelating agent.

Conjugate: A composite. As a verb, to join.

Derivatize: Modify a parent substance.

Labeling reagent: Substance to be reacted with a biomolecule that confers an additional property on said biomolecule wherein said biomolecule can be detected, tracked or monitored.

Polyaminopolycarboxylate: Compound, used often as a chelating agent, characterized by a plurality of amino groups and a plurality of carboxyl groups.

Product: The resulting substance of a reaction between or among reactants.

Reactant: Ingredient of a reaction, for example, a biomolecule is mixed with a labeling reagent to produce a conjugate, said biomolecule and said labeling reagent are two reactants of that reaction, and said conjugate is the product.

Unbound Reactant: Reactant that is not physically attached to another substance.

The invention turns on the use of chelator or chelating polymer conjugated to an inert matrix, preferably a particulate matrix, to scavenge unbound labeling reagent. The chelating agent is selected to have high avidity and high affinity for lower molecular weight compounds of which many labeling reagents are. Suitable chelating agents include ethylenediaminetetraacetic acid (EDTA), diethylenetriaminepentaacetic acid (DTPA), poly-azamacrocyclics, benzyl DTPA, benzyl EDTA, LiLo, IDAC, other activated derivatives of polyaminopolycarboxylates, some antibiotics, crown ethers, other macrocyclic compounds, natural chelating proteins such as transferrin, apoferritin and metallothionein, and diazotized aromatic amines. Chelating polymer and other multi-functional chelators may prove even more effective than those mentioned above.

Suitable matrices include glass, polystyrene, amine derivatized polymers, silica, agarose, silica propylamine, copolymers and other resins. With certain matrix-chelator combinations, the attachment of the chelating agent to the matrix does not require a complex reaction. Polystyrene and glass for example, have an inherent binding capacity for small molecules, proteins and the like. However in the case of amine derivatized polymer beads or amine derivatized polymer-coated glass beads, the chelators can be linked chemically to the beads.

Chelators can be synthesized on a matrix. By way of example, amine derivatized beads, available commercially, are packed into a column. The beads are coupled to iminodiacetate groups by simple carboxymethylation and the column is flushed with buffer. The beads are treated with ammonia, the column flushed and then again subjected to the carboxymethylation step. The process is repeated until the desired number of carboxylate groups are obtained.

The invention is suitable particularly for procedures that require biomolecules labeled with metals. It is not uncommon for the biomolecules to be labeled using a chelating agent bridge, i.e., the chelating agent is conjugated to the biomolecule, and the conjugate is then loaded with a metal wherein the metal is bound by the chelating agent. Suitable metals include α-and β-emitting radionuclides, γ-emitters, x-ray emitters, positron emitters, paramagnetic metal ions, luminescent and fluorescent metals. To further exemplify the range of elements and isotopes that can be used, suitable candidates include $^{56}Fe$, $^{54}Fe$, $^{55}Co$, $^{52}Fe$, $^{43}Sc$, $^{44}Sc$, $^{47}Sc$, $^{123}I$, $^{125}I$, $^{130}I$, $^{131}I$, $^{133}I$, $^{135}I$, $^{86}Rb$, $^{134}Cs$, $^{101}Rh$, $^{203}Pb$, $^{137}Cs$, $^{133}Ba$, $^{88}Y$, $^{90}Y$, $^{152}Eu$, $^{67}Ga$, $^{68}Ga$, $^{51}Cr$, $^{225}Ac$, $^{32}P$, $^{72}As$, $^{153}Sm$, $^{186}Re$, $^{199}Au$, $^{105}Rh$, $^{72}Se$, $^{97}Ru$, $^{100}Pd$, $^{109}Pd$, $^{119}Sb$, $^{128}Ba$, $^{197}Hg$, $^{211}At$, $^{212}Bi$, $^{212}Pb$, $^{213}Bi$, $^{188}Re$, $^{142}Pr$, $^{107}As$, $^{111}In$, $^{67}Cu$, $^{75}Br$, $^{77}Br$, $^{11}C$, $^{14}C$, $^{13}N$, $^{15}O$, $^{35}S$, $^{18}F$, Pr, Nd, $^{0159}Gd$, $^{166}Ho$, $^{194}Ir$, Sm, Eu, Gd, Tb, Dy, Ho, Er, Tm, Yb, $^{99m}Tc$, $^{192}Ir$ and $^{291}Am$, although it is preferable when using a chelator that the species be a cation.

A particular advantage is realized when the same species of chelating agent is conjugated both to the biomolecule and to the matrix. Because of no difference in affinity, there is little chance that the separation process will remove labeling reagent once bound to the biomolecule. To assist in visualizing some of the combinations in which chelators are conjugated to matrix and biomolecule, consider the following formulae:

BM—A—L

M—B—L wherein BM is a biomolecule;
M is a matrix;
A is a first chelator;
B is a second chelator; and
L is a label.

With K representing binding affinity, several comparisons can be symbolized in the following manner:

$A = B$ (1)

$A \neq B$ and $K_A = K_B$ (2)

$K_A > K_B$ (3)

$K_A < K_B$ (4)

In another embodiment of the scavenging procedure, three chelators are used with the additional component designated as:

M—C—L wherein C is a third chelator, and BM—A—L, M—B—L and M—C—L are used simultaneously in the procedure. Chelators B and C either are both conjugated to the same matrix or are each conjugated to a separate matrix. Comparisons relating to the latter embodiment include:

$A = B$ and $K_C < K_A$ (5)

$K_B < K_A$ and $K_C < K_A$ (6)

$K_B = K_A$ and $K_C < K_A$ (7)

As mentioned hereinabove, comparison (1) wherein the same chelator is conjugated to the biomolecule and to the matrix is a preferred combination. Comparison (2) is equivalent functionally to comparison (1). The efficiency of purification represented by comparison (3) depends on how much lower $K_B$ is from $K_A$. Apparent deficiencies may be remedied with increasing amounts of M—B—L. Comparison (4) is acceptable if $K_A$ is not much less than $K_B$. Comparisons (5), (6) and (7) may provide unexpected benefits with certain chelators.

Figure 1:
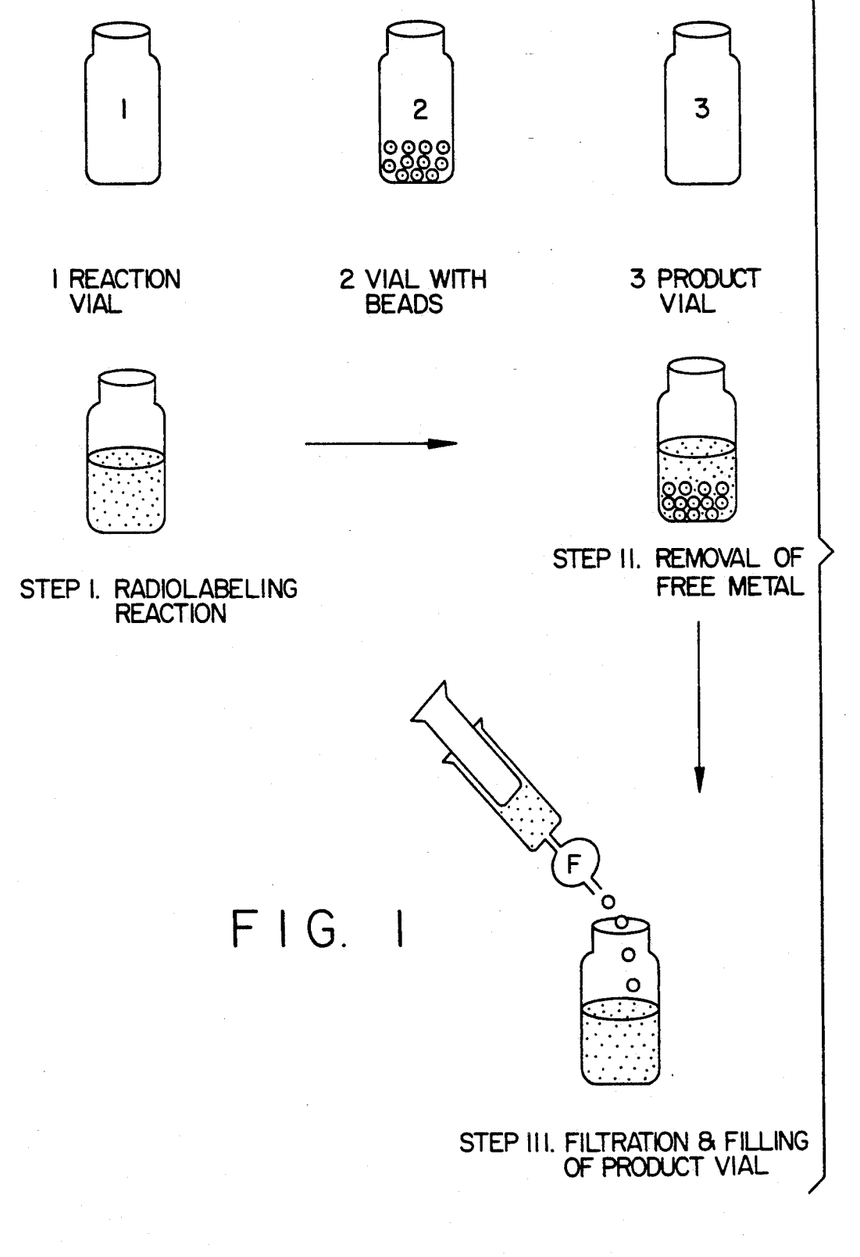
FIG. 1 depicts the use of a plurality of vessels to carry out the invention.

The labeling procedure can be performed in one or more sealed reaction vessels or in a multiple-chambered single reaction vessel. FIG. 1 diagrams an embodiment requiring multiple vessels, comprising, a first reaction vial, a second vial containing chelator attached matrix and a third product vial. Radiolabeling occurs in the first vial, the reaction mixture is removed to the second vial wherein said mixture contacts the chelator-matrix conjugate, thereafter the supernatant is removed, for example by means of a syringe, and said supernatant, which may be filtered, is collected in the third vial.

Figure 2:
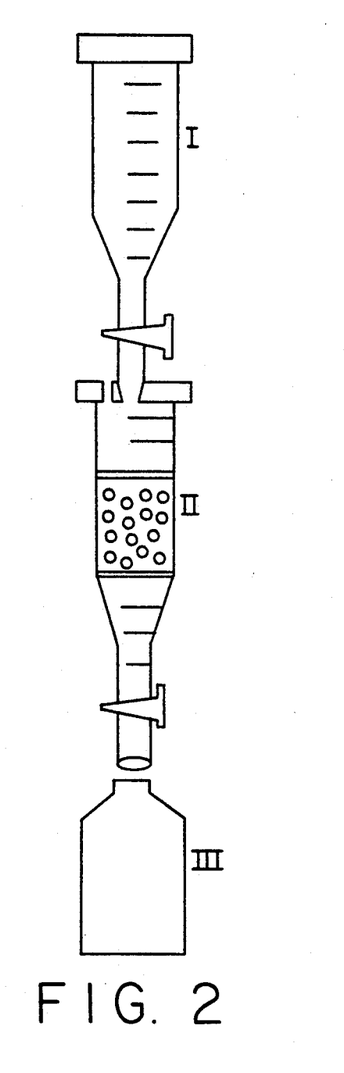
FIG. 2 depicts another embodiment comprising a single vessel with a plurality of compartments.

FIG. 2 illustrates another embodiment in which a single vessel with multiple compartments is represented. Said compartments are separated from each other by means for permitting transfer of reaction mixture from a first compartment (I) to a second adjacent compartment (II) containing chelator attached matrix. In this embodiment a valve device, e.g. a stopcock, separates the compartments. Equivalents of the stopcock include rupturable non-permeable membranes, moveable stoppers and scored glass. The third compartment (III) which receives the reaction mixture after the unbound labeling reagent is removed from the reaction mixture by the chelator-matrix conjugate, may be attached to said second compartment.

A third embodiment uses a sealed two compartment vessel. (Examples of sealed two compartment vessels that may be used in the invention are shown in *In re Sponnoble*, 160 USPQ 237.) The labeling reaction is conducted in the first compartment, into which the reactants are introduced, for example, by a syringe. The second compartment contains a chelator-matrix. After the labeling reaction is complete, a stopper means separating the first compartment and the second compartment is breached and the reactants are contacted with the chelator-matrix in the second compartment. After sufficient time for unbound label to be captured by the chelator-matrix, the labeled biomolecule in the supernatant may be removed using a syringe. Because the entire procedure takes place in a sealed, sterile vessel, the supernatant may be administered directly to a patient. The size of the matrix bound to the chelator, e.g. polymer beads, would be selected to be too large to enter the syringe.

Figure 3:
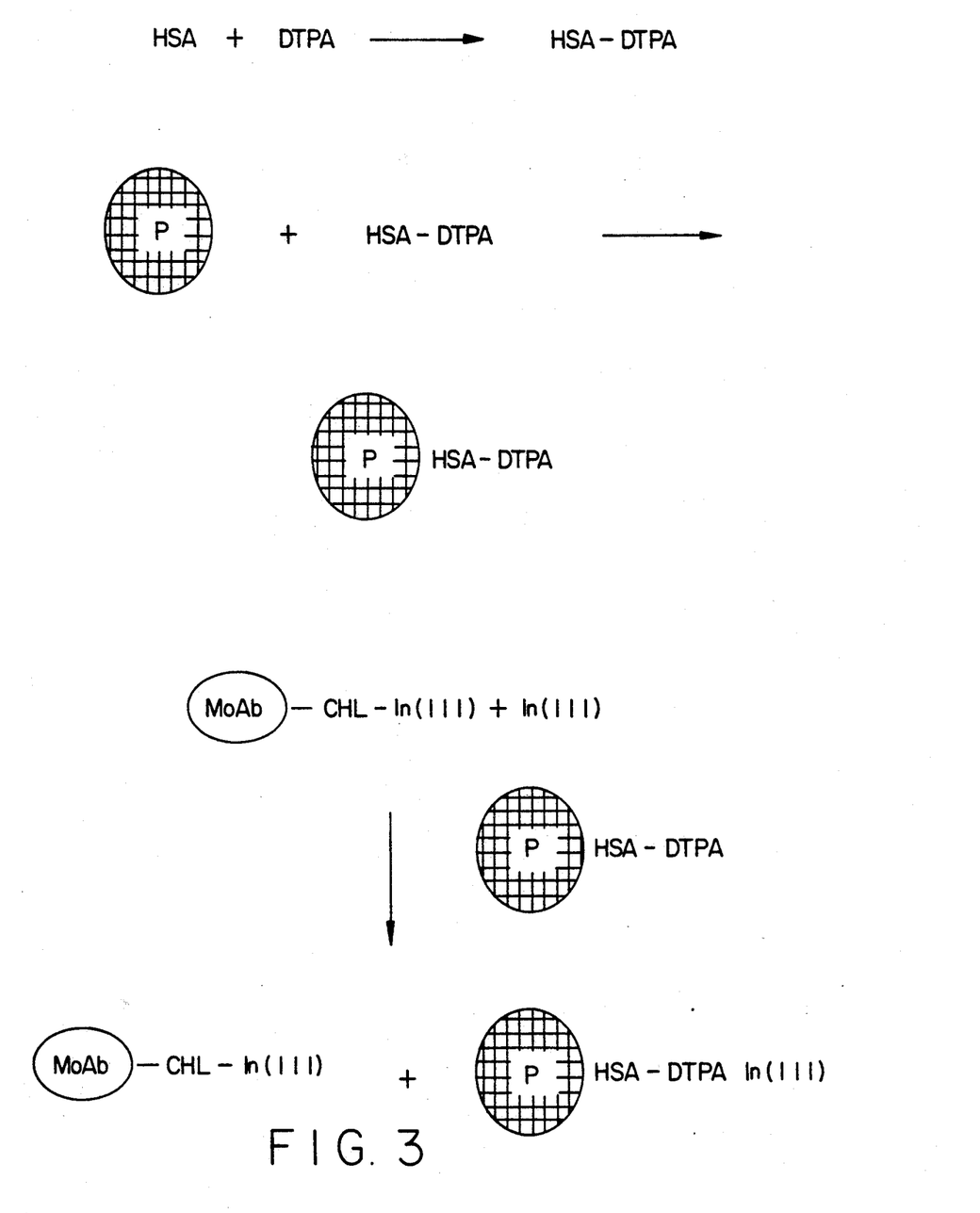
FIG. 3 depicts a method for making chelator attached matrix.

Appropriate matrices are selected and conjugated with a chelating agent. FIG. 3 is an example of preparing beads by indirect coupling. Human serum albumin (HSA) and diethylenetriaminepentaacetate (DTPA) are conjugated. The HSA-DTPA conjugate is attached to a particulate polymer matrix (P) to form P-HSA-DTPA. In another reaction vial, a chelator (CHL), in this example preferably DTPA, is conjugated to a monoclonal antibody (MoAb). The MoAb-CHL conjugate is labeled with indium (In(111)). In the figure unbound labeling reagent is denoted as In(III) and labeled antibody as MoAb-CHL-In(111). P-HSA-DTPA is added to the reaction mixture to scavenge In(111) by chelation.

Figure 4:
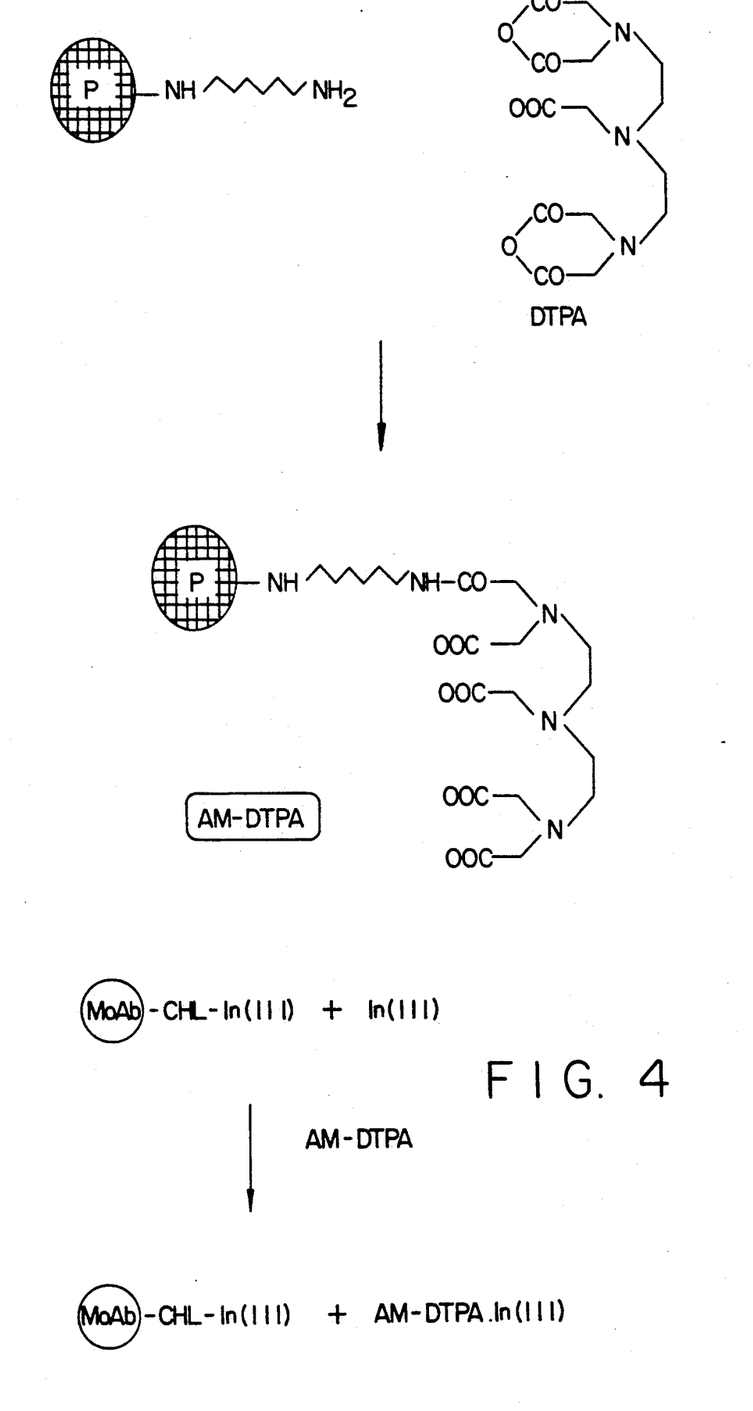
FIG. 4 depicts an alternative method for preparing chelator attached matrix.

FIG. 4 is another embodiment wherein beads and chelator are coupled directly. Alkylamine derivatized particulate polymer matrix (P—NH . . . ) is conjugated with DTPA to form AM-DTPA. In a fashion similar to that depicted in FIG. 3, AM-DTPA scavenges In(111) from the reaction mixture.

To further minimize non-specific binding to the matrix, the conjugates can be exposed to a proteinaceous or carbohydrate material to block those non-specific sites. Suitable blocking agents include bovine serum albumin, human serum albumin, sera, polyvinylpyrrolidone, dextran and ficoll. The chelator-matrix conjugates are washed thoroughly and an appropriate quantity is charged into a first vessel or into a chamber of said multiple-chambered vessel.

The biomolecule is conjugated with a chelating agent, preferably the same species as that conjugated to the matrix. Following the conjugation step, the biomolecule is separated from the unconjugated chelating agent by, for example, precipitation or gel exclusion chromatography. The resulting solution is charged into a second vessel or into a separate chamber of said multiple-chambered vessel. The labeling reagent, which generally is purchased from commercial vendors, is then introduced into the biomolecule-containing solution and chelation allowed to proceed under appropriate incubation conditions. In the next step, the labeling reaction solution is removed to the vessel or chamber con-taining the chelator-matrix conjugate. The final mixture is incubated with periodic mixing. The supernatant containing the labeled biomolecule is removed.

Alternatively, the biomolecule which serves as the effector molecule, for example, the antibody or nucleic acid probe, need not be labeled with an agent that in itself is detectable. Instead, said effector molecule is labeled with a first binding partner molecule and the detectable labeling agent is conjugated to a second binding partner molecule, wherein said first and second binding partner molecules react with each other to form a conjugate. That alternative labeling method is known as pretargeting. For example, tissue-reacted streptavidin-conjugated antibody may be visualized using radiolabeled biotin and a hybridized nucleic acid probe containing a poly-A tail may be visualized with an alkaline phosphatase conjugated poly-T oligonucleotide and appropriate phosphatase substrate such as NBT/BCIP. In the first antibody example, streptavidin and biotin are the first and second binding partner molecules and in the second nucleic acid example, poly-A and poly-T polynucleotides are the first and second binding partner molecules. Polymers that may be used as binding partner molecules include poly-N-vinylpyrrolidone, polyvinyl alcohols, polyethylene oxide and poly-N-vinylpyridine which reacts with polyacrylic acids and polymethacrylic acids.

The following non-limiting examples further illustrate and show aspects of the instant invention.

EXAMPLE 1

Polystyrene beads were conjugated with DTPA in a two-step method. Human serum albumin (HSA) in 50 mM phosphate-buffered saline, pH 7.2 was incubated with a 100-fold molar excess of DTPA dianhydride at room temperature for 15 minutes. Unconjugated DTPA was removed by passing the mixture over a G 50 column.

The HSA-DTPA solution was adjusted to 14 mg/ml and about 40 quarter inch, spherical, non-porous beads were added to the solution. The mixture was incubated with gentle shaking at room temperature for 2 hours. The liquid was decanted, the beads washed with distilled water and dried under vacuum.

EXAMPLE 2

A 0.1 mg/ml solution of DTPA anhydride in dry chloroform was prepared and an aliquot containing the desired quantity of DTPA was added to a reaction vessel. The chloroform was removed by evaporation with nitrogen gas at room temperature. A pH 7.0 solution of antibody (approximately 0.5 mg) in 0.05M bicarbonate buffer was added to said reaction vessel to produce a 7:1 molar ratio of anhydride to protein. The solution was incubated with shaking for one minute and the coupled antibody was recovered by passage over a Sephadex G-50 column.

EXAMPLE 3

The radionuclide was made 0.5 M in acetate, using 1.0M acetate, with a final pH of 6.0. The radionuclide solution was added to the antibody-DTPA conjugate along with 0.1 ml of 25% human serum albumin and the mixture was incubated for 5–30 minutes with frequent stirring.

EXAMPLE 4

HSA-DTPA beads were added to a solution containing $^{111}$In in acetate/citrate buffer in a total volume of 0.75 ml for about 30 minutes. The solution was removed and the radioactivity bound to the beads was determined.

| Number of Beads | Radioactivity in $\mu$Ci |
| --- | --- |
| 5 | 22 |
| 12 | 30 |
| 20 | 62 |

There is a direct correlation between the number of beads and the amount of bound radioactivity. Also, washing the beads with 1M HCl removed all bound radioactivity, enabling the beads to be reused.

EXAMPLE 5

HSA-DTPA was labeled with $^{111}$In in citrate/acetate buffer as described above. An aliquot was removed and treated with excess DTPA. Said DTPA-treated aliquot was analyzed by thin layer chromatography to determine percent free $^{111}$In. The aliquot contained 12.2% free $^{111}$In. Five HSA-DTPA beads were added to the HSA-DTPA-In $^{111}$In solution and the mixture was incubated at room temperature for 30 minutes. An aliquot was removed from that mixture, treated with excess DTPA and analyzed by TLC for free $^{111}$In. Said second aliquot contained 3.9% free $^{111}$In.

EXAMPLE 6

LiLo is a novel chelator developed at OTC/Bionetics Research Institute and is described in copending U.S. Application Ser. No. 07/720,277, filed Jun. 24, 1991, which is a continuation of U.S. application Ser. No. 07/43,558, filed Nov. 17, 1989, now abandoned which is a continuation-in-part of U.S. application Ser. No. 07/358,917, filed May 26, 1989, now abandoned. The chelator was attached to amine derivatized (AM) beads by exposing 60 AM beads to 5 ml of a saturated solution of LiLo prepared in water or in phosphate-buffered saline, pH 7.2. The pH of the mixture was adjusted to 7.5–8.5 using NaOH. The solution was stirred overnight at room temperature. The liquid was decanted and 1 M HCl was added to the beads. The mixture was incubated at room temperature for 10 minutes. That step removes free metal bound to LiLo-conjugated AM beads. The beads were rinsed repeatedly with 0.1M HCl. That was followed by distilled water rinses until the wash was neutral to pH paper. The beads were dried under vacuum and stored in a dessicator.

The structure of LiLo is as follows:

n=1, "a" LiLo1
n=2, "b" LiLo2.

EXAMPLE 7

Two hundred microcuries of indium chloride was combined in an acid-washed reaction vial with 15 μl of ace-tate buffer (0.6M, pH 5.5) and 15 μl of citrate buffer (0.06M, pH 5.5). Antibody-DTPA conjugate (157 μg in phosphate-buffered saline, pH 7.2) was added to the solution and the mixture was incubated at room temperature for about 30 minutes. Then, about 1 ml of phosphate-buffered saline (0.05 M, pH 7.2) was added. An aliquot of the reaction mixture was treated with excess DTPA solution to determine the percentage of unbound Indium-111 in the reaction mixture. To the remaining reaction solution, eight AM-LiLo beads were added. After incubating with the beads for about 30 minutes, an aliquot of the reaction solution was treated with excess DTPA. A chromatographic analysis was carried out to determine the percentage of unbound Indium-111 with the following results:

| Method | Percent of Indium-111 bound to the antibody |
| --- | --- |
| Before Beads | 83.0% |
| After Beads (AM-LiLo) | 99.7% |

EXAMPLE 8

IDAC-2 is a novel chelator developed at OTC/BRI and described in copending U.S. patent application Ser. No. 07/358917. IDAC-2 was conjugated to AM beads according to the method described in Example 7.

Although the foregoing disclosure describes the instant invention in detail by way of illustration for purposes of enablement and preferred embodiments, one having ordinary skill in the art will know that changes, modifications and other uses can be made, and are available, without departing from the scope and spirit of the invention. The scope of the invention is, therefore, indicated by the appended claims and any change that comes within the meaning and range of equivalency of the claims are to be embraced within the scope.

What is claimed is:

1. A method for scavenging unbound In or Y from a reaction mixture for labelling biomolecules comprising biomolecules bound through chelators to In or Y and unbound In or Y, comprising the step of contacting the reaction mixture with an insoluble chelator-matrix conjugate capable of binding unbound In or Y after the binding of In or Y to biomolecules is essentially complete, whereby unbound In or Y is bound to the chelator-matrix and separated from the reaction mixture, wherein the chelator in the insoluble chelator-matrix is LiLo.

2. The method of claim 1 wherein said biomolecule is a peptide or a protein.

3. The method of claim 2 wherein said protein is an immunoglobulin or an immunoglobulin fragment.

4. The method of claim 1 wherein said biomolecule is a nucleic acid, an oligonucleotide or a polynucleotide.

5. The method of claim 1 wherein said In or Y is a radionuclide.

6. The method of claim 1 wherein said matrix is particulate.

7. The method of claim 1 wherein said matrix is derivatized.

8. The method of claim 1 wherein said matrix comprises the inside surface of a vessel.

9. The method of claim 1 wherein said matrix is a membrane.

10. A kit, comprising a sterile vessel containing a LiLo-matrix conjugate, a second vessel containing a chelator-immunoglobulin conjugate, a means for contacting the two conjugates, and a means for separating the two conjugates after contacting for performing the method of claim 1.

11. A kit comprising a sterile vessel having plurality of chambers and a chelator-matrix conjugate in one chamber and a chelator-immunoglobulin conjugate in a second chamber, wherein the chelator in the chelator-matrix is LiLo.

12. A method for preparing a sterile biomolecule composition labeled with In or Y essentially free of unbound In or Y for administration to a patient comprising the steps of:
  (a) contacting a biomolecule chelating moiety conjugate with In or Y in a reaction mixture in a sterile vessel and permitting the In or Y to bind to the biomolecule through the chelating moiety; and
  (b) contacting the mixture of step (a) with an insoluble chelator-matrix conjugate capable of binding unbound In or Y in an amount sufficient to bind essentially all unbound In or Y, wherein the chelator in the chelator-matrix conjugate is LiLo, whereby a solid phase containing bound In or Y and a liquid phase containing labeled biomolecules are produced and the liquid phase is separated from the solid phase by phase separation.

13. The method of claim 12 wherein said biomolecule is an immunoglobulin.

14. The method of claim 12 wherein the In or Y is radioactive.

15. The method of claim 12 wherein the liquid phase containing labeled biomolecules is separated from the solid phase by means of a syringe and the chelator-matrix conjugate is too large to be syringed.

16. The method of claim 12 wherein steps (a) and (b) are carried out in separate reaction vessels and the reagents are introduced and withdrawn with a syringe.

17. The method of claim 12 wherein steps (a) and (b) are carried out in separate compartments of a single vessel and said compartments are interconnected by a means permitting transfer of contents between compartments.

18. The method of claim 17 which further comprises a third compartment which is connected to said second compartment, wherein said second and third compartments are interconnected by a means for permitting transfer of contents between compartments.

19. The method of 17 wherein the means permitting transfer of contents between compartments is blocked by a removable blocking means.

* * * * *